US00PP22455P2

(12) United States Plant Patent
Delabroye

(10) Patent No.: US PP22,455 P2
(45) Date of Patent: Jan. 10, 2012

(54) ***GERANIUM* PLANT NAMED 'MIDNIGHT BLUES'**

(50) Latin Name: ***Geranium* hybrid**
Varietal Denomination: Midnight Blues

(76) Inventor: Sandrine Delabroye, Hantay (FR)

( * ) Notice: Subject to any disclaimer, the term of this patent is extended or adjusted under 35 U.S.C. 154(b) by 0 days.

(21) Appl. No.: 12/807,263

(22) Filed: Sep. 1, 2010

(51) Int. Cl.
*A01H 5/00* (2006.01)
(52) U.S. Cl. ..... Plt./324
(58) Field of Classification Search ..... Plt./324
See application file for complete search history.

*Primary Examiner* — Susan McCormick Ewoldt
(74) *Attorney, Agent, or Firm* — Penny J. Aguirre

(57) ABSTRACT

A new cultivar of hybrid *Geranium,* 'Midnight Blues', characterized by its dark purple foliage, its dark purple, its large leaves, sturdy leaves, and its vigorous growth habit compared to typical dark-foliaged *Geranium* cultivars.

2 Drawing Sheets

Botanical classification: *Geranium* hybrid.
Cultivar designation: 'Midnight Blues'.

BACKGROUND OF THE INVENTION

The present invention relates to a new and distinct cultivar of *Geranium* plant, botanically of hybrid origin and known as *Geranium* 'Midnight Blues' and will be referred to hereafter by its cultivar name, 'Midnight Blues'.

The inventor discovered the new cultivar, 'Midnight Blues', as a naturally occurring a whole plant mutation in a cultivated growing area at his nursery in Hantay, France in summer of 2008. The parentage of 'Midnight Blues' is unknown, however the parents are likely to be a *Geranium* 'Midnight Reiter' (not patented) and *Geranium* 'Hocus Pocus' (not patented) based on their proximity in the growing area and the characteristics of the new cultivar.

Asexual reproduction of the new cultivar was first accomplished by in vitro propagation in Rijswijk, The Netherlands in 2009 under the direction of the Inventor. Repeated asexual reproduction has determined that the characteristics of this cultivar are stable and are reproduced true to type in successive generations.

SUMMARY OF THE INVENTION

The following traits have been repeatedly observed and represent the characteristics of 'Midnight Blues'. These attributes in combination distinguish 'Midnight Blues' as a new and distinct cultivar of *Geranium.*

1. 'Midnight Blues' exhibits foliage that is dark purple in color.
2. 'Midnight Blues' exhibits large blue flowers.
3. 'Midnight Blues' exhibits large leaves, sturdy leaves.
4. 'Midnight Blues' exhibits a vigorous growth habit in relation to typical dark-foliage *Geranium* cultivars.

'Midnight Blues' can be closely compared to its probable parents plants. 'Midnight Blues' differs from 'Midnight Reiter' in having leaves that are darker purple in color, larger in size, and sturdier. 'Hocus Pocus' differs from 'Midnight Blues' in having foliage that becomes green in the center of the foliage in summer and in having flowers that are light purple in color with white centers.

BRIEF DESCRIPTION OF THE DRAWING

The accompanying colored photographs illustrate the overall appearance and distinct characteristics of the new *Geranium.* The photographs were taken of a one year-old plant of 'Midnight Blues' as grown outdoors in a 3-liter container in The Netherlands.

The photograph in FIG. 1 is a side view of a plant of 'Midnight Blues' in bloom. The photograph in FIG. 2 is of a close-up view of the foliage of 'Midnight Blues' while the photograph in FIG. 3 provides a close-up view of the flowers of 'Midnight Blues'.

Figure 1:
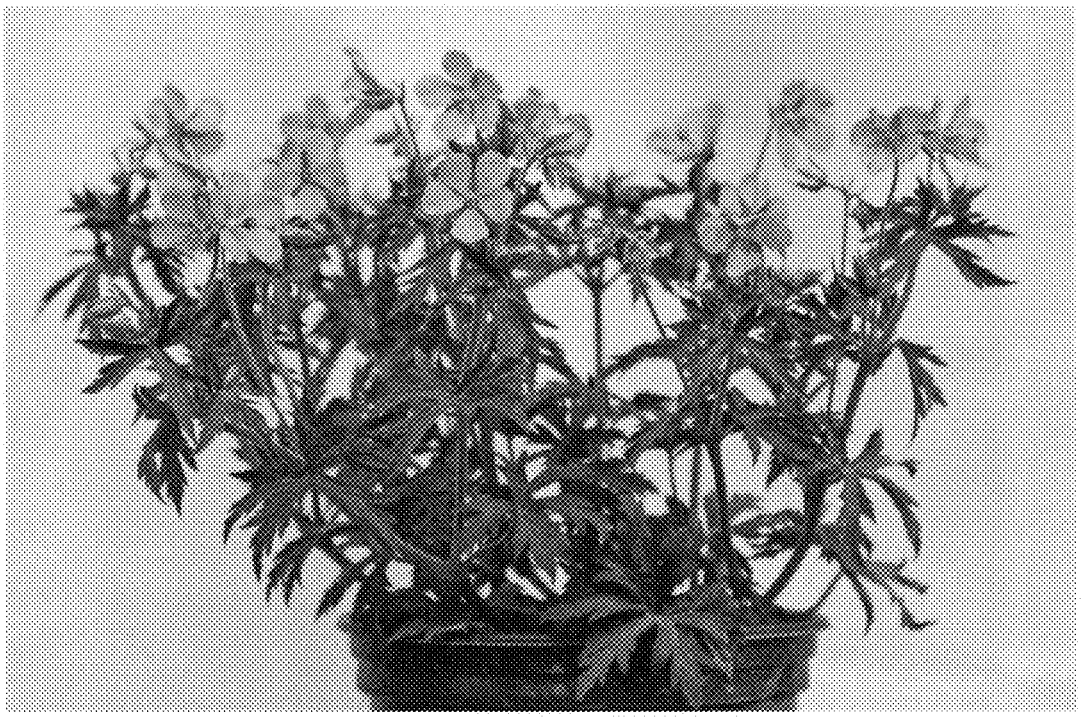
Figure 2:
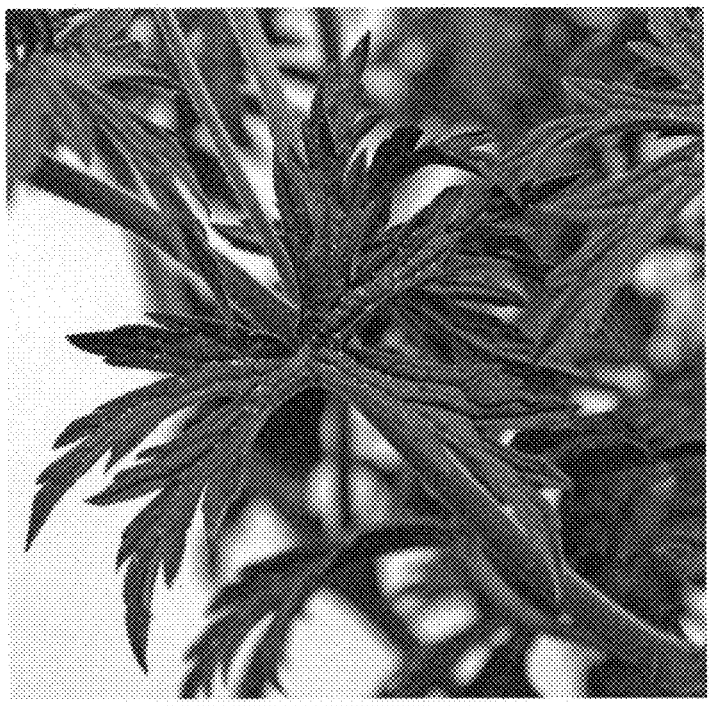
Figure 3:
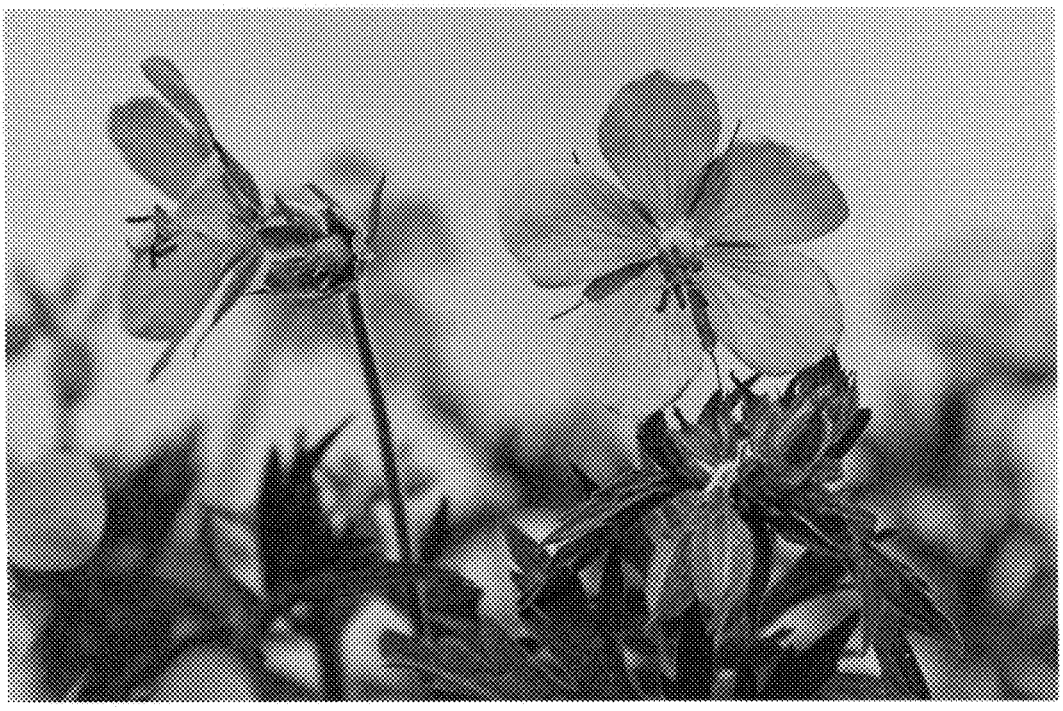

The colors in the photographs are as close as possible with the digital photography and printing techniques utilized and the color codes in the detailed botanical description more accurately describe the colors of the new *Geranium.*

DETAILED BOTANICAL DESCRIPTION OF THE PLANT

The following is a detailed description of 1 year-old, field grown plants of the new cultivar as grown outdoors in Noordwjik, The Netherlands, with day temperatures ranging from 12° to 23° C. and night temperatures ranging from 5° to 17° C. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

General characteristics:

*Blooming period.*—Early May to late September in The Netherlands.

*Plant habit.*—Herbaceous perennial with an upright, broadly spreading growth habit.

*Height and spread.*—Reaches about 25 cm in height and about 35 cm in spread.

*Cold hardiness.*—At least to U.S.D.A. Zone 5.

*Heat tolerance.*—At least tolerant to temperatures up to 35° C.

*Diseases and pests.*—No susceptibility or resistance to diseases or pests has been observed.

*Root description.*—Fibrous roots extending from stout rootstock.

*Branching habit.*—Moderately branched, about 11 lateral branches on a 1 year-old plant.

Growth and propagation:

*Growth rate.*—Vigorous relative to dark-foliaged *Geraniums,* growth rate in stems is about 10 cm per month.

*Propagation.*—In vitro propagation preferred.

Stem description:

*Stem size.*—Average of 15.9 cm in length and 4 mm in width.

*Stem shape.*—Round.

*Stem color.*—Young stems and under sides of mature stems 176A tinged with 144B, upper surface of mature stems and old stems 178A.

*Stem surface.*—Moderately glossy, pubescent with soft hairs 0.5 mm in length.

*Stem strength.*—Moderately strong.

*Internode length.*—Average of 5.9 cm.

Foliage description:

*Leaf shape.*—Orbicular, palmately cleft with an average of 5 lobes.

*Leaf division.*—Simple.

*Leaf base.*—Hastate.

*Leaf apex.*—Acute.

*Leaf venation.*—Palmate, upper surface 147A in color strongly tinged with N186A, lower surface 148B.

*Leaf margins.*—Palmately parted, lobes serrate.

*Leaf attachment.*—Petiolate.

*Leaf arrangement.*—Opposite.

*Leaf surface.*—Upper surface is dull and sparsely covered with short hairs about 0.5 mm in length, lower surface is pubescent only on veins.

*Leaf color.*—Young and mature upper surface; 147A margins strongly tinged N186A, young lower surface; N186C, base 147B, mature lower surface; N187B, base 146A and 146B.

*Leaf size.*—Average of 6.1 cm in length and 7.6 cm in width.

*Leaf quantity.*—Average of 6 per lateral branch.

*Petiole size.*—Average of 2.8 cm in length and 2 mm in width.

*Petiole color.*—183B.

*Stipules.*—Two at each node, narrow ovate to narrow deltoid in shape, average of 9 cm in length and 3 mm in width, 183B to 184B.

Flower description:

*Inflorescence type.*—Single, rotate, arranged in pairs.

*Flowering period.*—Late spring to late summer.

*Lastingness of flowers.*—About 7 days, self cleaning.

*Flower size.*—Average of 1.1 cm in depth and 3.2 cm in diameter.

*Flower fragrance.*—None.

*Flower number.*—Average of 20 buds per lateral branch (10 pairs), about 240 per plant, with 15% open at any stage.

*Flower aspect.*—Outward to slightly upright.

*Flower bud size.*—Average of 1.1 cm in length, up to 4 mm in width.

*Flower bud color.*—148B, with stripes of N200A.

*Flower bud surface.*—Densely covered with short glandular hairs; 0.7 mm in length and 156D in color.

*Flower bud shape.*—Ovate.

*Corolla features.*—Petals are un-fused and arranged in a rotate form.

*Petal number.*—5.

*Petal shape.*—Obcordate.

*Petal color.*—Upper and lower side of opening and mature petals; a blend of N88B and 92A, base N88C, veins N80B, upper and lower sides of fading petals; N81B, base 76B and 76C, veins N80C.

*Petal surface.*—Smooth, velvety, sparsely covered with hairs 0.5 mm in length, NN155D in color.

*Petal margins.*—Entire.

*Petal apex.*—Rounded.

*Petal size.*—Average of 1.7 cm in length and 1.1 cm in width.

*Calyx form.*—Rotate, slightly cupped.

*Calyx size.*—Average of 7 mm in length and 2.1 cm in diameter.

*Sepal number.*—Average of 5.

*Sepal shape.*—Ovate to narrowly ovate.

*Sepal margin.*—Entire.

*Sepal size.*—Average of 1.2 cm length and 4 mm in width.

*Sepal surface.*—Dull, glabrous.

*Sepal apex.*—Mucronate.

*Sepal base.*—Cuneate.

*Sepal color.*—Immature and mature upper side 148A, immature and mature lower side; 148A with stripes N199B.

*Peduncle size.*—Average of 6.4 cm in length and 1.5 mm in diameter.

*Peduncle strength/aspect.*—Moderate to strong, held at about a 45° angle relative to lateral branch.

*Peduncle shape.*—Slightly ovoid.

*Peduncle color.*—174A to 174B.

*Pedicel size.*—Average of 0.5 cm in length and 1 mm in width.

*Pedicel shape.*—Slightly ovoid.

*Pedicel strength/aspect.*—Moderately strong, lateral flowers are held at about 30° relative to peduncle.

*Pedicel color.*—174A to 174B.

Reproductive organs:

*Gynoecium.*—1 pistil, about 9 mm in length, 5 stigmas are decurrent and 184C in color, style is about 7 mm in length and 184A to 184B in color, ovary is 145A in color.

*Androcoecium.*—10 stamens, anthers are dorsifixed, oblong in shape, 2 mm in length, 0.5 mm in width, and 203B in color, filament is 6 mm in length and 186B to 186C in color, pollen is low in abundance and 160C in color.

*Fruit/seeds.*—No fruits or seeds observed.

It is claimed:

1. A new and distinct cultivar of *Geranium* plant named 'Midnight Blues' as herein illustrated and described.

* * * * *